(12) United States Patent
Kaushal et al.

(10) Patent No.: US 8,406,839 B2
(45) Date of Patent: Mar. 26, 2013

(54) METHOD AND APPARATUS FOR DETERMINING BLOOD ANALYTES

(75) Inventors: Ashwani Kaushal, Mississauga (CA); Duncan MacIntyre, Campbellville (CA)

(73) Assignee: Covidien LP, Mansfield, MA (US)

( * ) Notice: Subject to any disclaimer, the term of this patent is extended or adjusted under 35 U.S.C. 154(b) by 1380 days.

(21) Appl. No.: 11/885,537

(22) PCT Filed: Mar. 3, 2006

(86) PCT No.: PCT/CA2006/000301
§ 371 (c)(1),
(2), (4) Date: Apr. 15, 2008

(87) PCT Pub. No.: WO2006/092050
PCT Pub. Date: Sep. 8, 2006

(65) Prior Publication Data
US 2008/0198361 A1 Aug. 21, 2008

Related U.S. Application Data

(60) Provisional application No. 60/658,563, filed on Mar. 4, 2005.

(51) Int. Cl.
*A61B 5/00* (2006.01)
(52) U.S. Cl. .................................................. 600/322
(58) Field of Classification Search ............... 600/326, 600/322, 323
See application file for complete search history.

(56) References Cited

U.S. PATENT DOCUMENTS

| | | | | |
|---|---|---|---|---|
| 5,361,758 | A | 11/1994 | Hall et al. | 128/633 |
| 5,991,023 | A | 11/1999 | Morawski | 356/326 |
| 6,002,479 | A | 12/1999 | Barwitz et al. | 356/326 |
| 6,040,578 | A | 3/2000 | Malin et al. | 250/339.12 |
| 6,236,047 | B1 * | 5/2001 | Malin et al. | 250/339.12 |
| 6,365,363 | B1 | 4/2002 | Parfenov et al. | 435/11 |
| 6,708,048 | B1 * | 3/2004 | Chance | 600/322 |
| 6,859,658 | B1 * | 2/2005 | Krug | 600/323 |
| 7,613,488 | B1 * | 11/2009 | Maracas et al. | 600/322 |
| 2004/0054270 | A1 * | 3/2004 | Pewzner et al. | 600/341 |
| 2004/0260165 | A1 * | 12/2004 | Cho et al. | 600/365 |

FOREIGN PATENT DOCUMENTS

WO WO 93/16629 9/1993

OTHER PUBLICATIONS

Carpenter, et al., pp. 134, in Cleland J., Langer R., eds. "Formulation and Delivery of Protein and Peptides", *Amer. Chem. Soc.* (1994).
Potts et al., "Glucose monitoring by reverse iontophoresis,"*Diabetes/Metabolism Research Reviews* 18:S49-S53 (2002).
Tierney et al., "Electroanalysis of glucose in transcutaneously extracted samples,"*Electroanalysis* 12(9):666-671 (2000).

* cited by examiner

*Primary Examiner* — Max Hindenburg

(57) ABSTRACT

The present invention provides a method of measuring the concentration of a compound and a value of oxygen saturation in the blood of a part of a subject. Also provided is a device for carrying out the disclosed method. The method relates to measuring the concentration of a compound and a value of oxygen saturation in the blood part of a subject, and correlating the measured concentration of the compound and/or the value of oxygen saturation in the blood to a specific clinical condition. The device comprises a polychromatic light source, a receptor, a detector, and a processing system comprising a calibration algorithm.

10 Claims, 3 Drawing Sheets

METHOD AND APPARATUS FOR DETERMINING BLOOD ANALYTES

CROSS-REFERENCE TO RELATED APPLICATIONS

The present application is a National Phase Application of International Application No. PCT/CA2006/000301, filed Mar. 3, 2006, which claims priority to U.S. Patent Application No. 60/658,563, filed Mar. 4, 2005, which applications are incorporated herein fully by this reference.

FIELD OF THE INVENTION

The present invention relates to a method of measuring the concentration of a compound and a value of oxygen saturation in the blood of a part of a subject, for example, a human or animal, and, optionally, of correlating the measured concentration of the compound and/or the value of oxygen saturation in the blood to a specific clinical condition or to the propensity for a specific clinical condition. The present invention also provide a device for carrying out the method.

BACKGROUND OF THE INVENTION

Non-invasive measurement of the concentration of a compound or analyte in a part of a subject, such as the finger, arm or earlobe, may be difficult in cases where there is interfering background absorption of the same, or other analytes, within the body part from non-target compartments. Changes in the volume of the different compartments may also adversely impact on readings obtained for the determination of a compound within a part of the body.

Compartments within tissue of the body may include, but are not limited to the vascular, interstitial, cellular, lymph, connective tissue, and bone compartments. In the case where the interfering background absorption is from the same analyte present in a non-target compartment, then the concentration of the analyte in the compartment of interest may be overestimated. Changes in the volume of different compartments within the light path, may effect the determination of the concentration of the compound. In order to determine the total amount of a compound within a body part, the occurrence of the compound within each of the compartments may be required. This may be important in cases where the relative amount of a compound of interest may vary within different compartments over time or as a result of a medical condition.

For example, when the method disclosed in U.S. Pat. No. 5,361,758 (Hall et al.) is used to measure the blood glucose concentration in diabetic patients adhering to an insulin regime, the background glucose concentration in the cells and the interstitial fluid is negligible and does not interfere significantly with the measured plasma glucose concentration. However, any excess glucose in the blood is eliminated through urination, resulting in dehydration of the patient as water is continuously removed from the tissues of the body and from the interstitial fluid. As a result of the decrease in the cellular and interstitial fluid volumes, the effective glucose concentrations in the cellular and interstitial compartments increases. The increase of glucose in non-target compartments can interfere with the measurement of the blood glucose concentration when using non-invasive measurement techniques, such as that disclosed in Hall et al. This overestimation can result in an inaccurate reading of blood glucose levels. The development of a process that is able to determine the concentration of a particular analyte in different compartments of a part of an individual is therefore of importance.

Clinical studies have revealed that the concentration of certain compounds in one particular compartment of a part of a subject, such as the skin, may be used to assess the risk of development of specific medical conditions in that subject. Early detection of these types of risks in a patient permits measures to be taken that may slow or even prevent the onset of these conditions. As an example, it has been determined that elevated concentrations of cholesterol in the skin of an individual is an indication of a risk for coronary disease. Therefore, the development of simple, non-invasive methods for determining the concentration of skin compounds is of importance.

In U.S. Pat. No. 6,365,363, Parfenov et al. describe a method of indirectly measuring the concentration of cholesterol in the skin of a subject by enzymatically oxidizing the cholesterol in a section of the subject's skin and then quantitating the amount of the hydrogen peroxide by-product stoichiometrically formed in this reaction using a second enzymatic reaction. As a complex series of enzymatic reactions are used in this method to indirectly determine the concentration of cholesterol, the method is both costly and prone to error. In addition, the development of a result using this method is time consuming.

In U.S. Pat. Nos. 6,236,047 and 6,040,578, Malin et al. describe a method for determining the concentration of a blood compound using light in the nearinfrared range by analysing diffusively reflecting radiation emerging from the irradiated sample. However, there is no teaching in these patents as to the determination of concentrations of constituents in the various compartments of a part of a subject.

Hall et al. also describe in U.S. Pat. No. 5,361,758 a non-invasive technique for directly measuring the concentration of constituents of blood using light in the near-infrared range. The glucose value is referenced with respect to the blood compartment only and the glucose concentrations obtained using this method may be prone to error arising from changes in the fluid content in other compartments.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to a method of measuring the concentration of a compound and a value of oxygen saturation in the blood of a part of a subject, for example, a human or animal, and, optionally, of correlating the measured concentration of the compound and/or the value of oxygen saturation in the blood to a specific clinical condition or to the propensity for a specific clinical condition. The present invention also provide a device for carrying out the method.

The present invention provides a device for measuring a concentration of one or more than one compound and a value of oxygen saturation of blood in a part of a subject, comprising:

a polychromatic light source that emits a wavelength of light in the visible red spectrum, a wavelength of light in the infrared spectrum and a broad spectrum of light in the near infrared range, the light source being operatively coupled to a power source;

a receptor for receiving a part of the subject and comprising one or more than one input in operable association with the polychromatic light source, one or more than one output in operable association with a dispersing element, and a control device for measuring a value of blood volume in the part or a pulse of the subject, the one or more than one input and the one or more than output defining a light path within the receptor, wherein, the part of the subject when received by the receptor is placed within the light path;

a detector for measuring transmitted or reflected light received from the dispersing element, the detector operatively coupled to a processing system;

the processing system comprising one, or more than one calibration algorithm for determining a concentration for the one or more than one compound and the value of oxygen saturation of blood in the part, and an algorithm for controlling the detector based on the value of blood volume or the pulse measured by the control device.

The present invention further provides a method for determining a concentration of a compound and a value of oxygen saturation of blood, in a part of a subject, comprising:

(a) directing a wavelength of light in the visible red spectrum, a wavelength of light in the infrared spectrum, and a broad spectrum of electromagnetic radiation (EMR) from the near-infrared spectrum onto the part;

(b) measuring a quantity of EMR reflected by, or transmitted through the part with a detector; and (c) performing a quantitative mathematical analysis of the quantity of EMR using an algorithm that accounts for concentration of the compound within one, or more than one compartment, and the volume of the part; and (d) determining the concentration of the compound and the value of oxygen saturation of blood in the part.

The present invention also provides a method for determining the concentration of a compound in one, or more than one, compartment and a value of oxygen saturation of blood of a part of a subject, comprising:

(a) directing a broad spectrum of electromagnetic radiation (EMR) from the near-infrared (NIR) spectrum onto the part;

(b) measuring a quantity of EMR reflected by, or transmitted through the part with a detector, and (c) performing a quantitative mathematical analysis of the quantity of EMR to determine the concentration of the compound in each of the one, or more than one, compartment and the value of oxygen saturation of blood of a part.

The present invention also provides a method for determining the concentration of a compound in compartments of a part of a subject, and a value of oxygen saturation of blood in a part of a subject, the method comprising the steps of:

(a) directing a broad spectrum of electromagnetic radiation (EMR) from the near-infrared (NIR) spectrum onto the part (b) measuring a quantity of EMR reflected by, or transmitted through the part with a detector, and (c) performing a quantitative mathematical analysis of the quantity of EMR, using algorithms for the compound within each compartment to determine the concentration of the compound in each compartment within the part and an algorithm to determine the oxygen saturation of blood in the part.

The present invention pertains to a method for determining a corrected concentration of a compound in a compartment and a value of oxygen saturation of blood of a part of a subject, comprising:

(a) directing a broad spectrum of electromagnetic radiation (EMR) from the near-infrared spectrum onto the part;

(b) measuring a quantity of EMR reflected by, or transmitted through the part with a detector;

(c) performing a quantitative mathematical analysis of the quantity of EMR using an algorithm for the compound and within the compartment and an algorithm for the value of oxygen saturation of blood of the part; and (d) determining the concentration of the compound in the compartment, and the value of oxygen saturation of blood of the part.

The present invention also provides a method of identifying a clinical condition in need of treatment in a human or animal, the method comprising the steps of:

(a) directing a broad spectrum of electromagnetic radiation (EMR) from the near-infrared spectrum onto the part;

(b) measuring a quantity of EMR reflected by, or transmitted through the part with a detector;

(c) performing a quantitative mathematical analysis of the quantity of EMR to determine the concentration of the compound in a compartment of the part and a value of oxygen saturation of blood in the part, wherein the mathematical analysis involves a step of determining a total concentration of the compound in the part, and a step of assigning a fraction of the total concentration to each compartment of the part, and (d) correlating the concentration of the compound in the compartment and/or the value of oxygen saturation of blood in the part to the clinical condition in need of treatment by using a correlation algorithm.

The present invention is also directed to a method to determine an algorithm for deriving a concentration of a compound in a part of a body comprising:

(a) measuring a concentration of the compound in two or more compartments within the part;

(b) directing electromagnetic radiation (EMR) over a set of wavelengths onto the part;

(c) measuring a quantity of EMR reflected by, or transmitted through the part with a detector for each wavelength of the set of wavelengths, to obtain a set of values;

(d) performing a statistical analysis wherein the concentration of the compound is the independent variable, and the set of values is the dependent variable, thereby determining the algorithm.

In a preferred embodiment, the compartment in the above-described methods is selected from the group consisting of a cellular, interstitial, lymphatic, bone, and blood compartment.

In another preferred embodiment, the compound in the above-described methods is selected from the group consisting of a fat, a protein, a glycoprotein, a lipoprotein, a carbohydrate (e.g. glucose), a steroid (e.g. cholesterol), an amino acid, nitrogen, carbon dioxide, cortisol, creatine, creatinine, a ketone, a lipid, urea, a fatty acid, glycosolated hemoglobin, alcohol, lactate, $Ca^{2+}$, $K^+$, $Cl^-$, $HCO_3^-$; $HPO_4^-$; low density lipoprotein, high density lipoprotein, BNP, troponin T and C-reactive protein.

By determining the concentration of a compound in different compartments within a part, a more accurate reading of the compound, either as a measure of the total amount of the compound, or as a corrected amount of the compound within a target compartment, is possible. This is especially true when the relative concentration of the compound varies within non-target compartments due to changes in the environment of the compartment, and an accurate reading of the compound in a target compartment, is required. The values determined of the compound in each compartment may be used to calculate the total amount of the compound in the body, they may be used as an indicator of the amount of compound within a compartment, or they may be used to calculate the amount of a compound in a target compartment This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DESCRIPTION OF PREFERRED EMBODIMENTS

Figure 1:
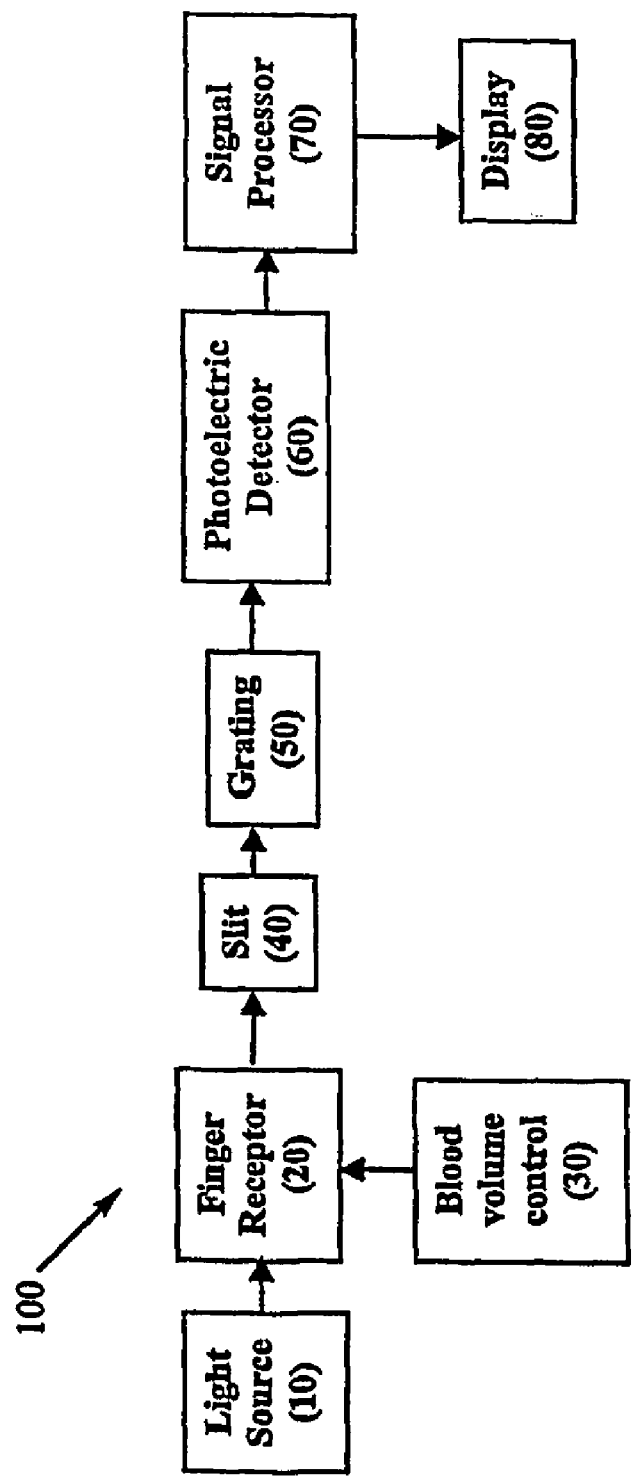
FIGS. 1-2 illustrate block diagrams of examples of a device according to the present invention, which measures both a concentration of one or more compounds and a value of oxygen saturation of blood in a part of a subject.

The present invention relates to a method of measuring the concentration of a compound and a value of oxygen saturation in the blood of a part of a subject, for example, a human or animal, and, optionally, of correlating the measured concentration of the compound and/or the value of oxygen saturation in the blood to a specific clinical condition or to the propensity for a specific clinical condition. The present invention also provide a device for carrying out the method.

The following description describes preferred embodiments by way of example only and without limitation to the combination of features necessary for carrying the invention into effect.

The expression "part of a subject", as used herein, refers to an element or section of a human or animal to which electromagnetic radiation (EMR) can be directed. The element or section can be, without limitation, an earlobe, a finger, an arm, a leg, torso, cheek, or a toe.

The term "compartment", as used herein, comprises a distinguishable portion of a tissue within a part of a human or animal. Examples of compartments, that are not to be considered limiting, include the vascular, interstitial, cellular, lymph, bone, and connective tissue, compartments. A compartment typically comprises fluid, for example, interstitial fluid, lymphatic fluid, the cytosol, and blood. Each of these compartments is capable of containing a biological compound such as, and without limitation to, a fat, a protein, a glycoprotein, a lipoprotein, a carbohydrate (e.g. glucose), a steroid (e.g. cholesterol), an amino acid, nitrogen, carbon dioxide, cortisol, creatine, creatinine, a ketone, a lipid, urea, a fatty acid, glycosolated hemoglobin, alcohol, lactate, $Ca^{2+}$, $K^+$, $Cl^-$, $HCO_3^-$; $HPO_4^-$, low density lipoprotein, high density lipoprotein, BNP, troponin T and C-reactive protein.

The present invention provides a device for non-invasive determination of the concentration of one or more compounds and a value of oxygen saturation of blood within a part a subject. The apparatus comprises a receptor shaped so that it can be placed in contact with a region of skin from a subject. A source of electromagnetic radiation (EMR) is fed into the receptor, and following interaction with one or more than one compounds within the body part, the EMR is collected and analyzed. The device may comprise an apparatus as known in the art, for example, but not limited to those disclosed in U.S. Pat. No. 5,361,758, WO 93/16629, U.S. Pat. No. 6,236,047 or 6,040,578 (all of which are incorporated herein by reference). The EMR that is collected after interaction with compounds within the part of the subject may be either reflected from, transmitted through, or both reflected from and transmitted through the part of the subject depending upon the apparatus used. The collected EMR signal is processed using one or more than one calibration algorithms to determine the concentration of one, or more than one target compounds within the target part, and the value of oxygen saturation of blood in the part.

In an aspect of the present invention, a part may be the skin, and the skin of a subject can be brought into contact with a receptor for measurement of one or more compounds within the skin. If a total analysis of compound is desired, a receptor may be placed, or pressed, against the skin and used to determine the concentration of a compound within all of the compartments of the skin. However, it may be desired that the blood content of the skin within the sample area be reduced, for example if the concentration of a compound in non-blood compartments is to be determined. If reduced blood content of the skin is desired, the skin may be lightly pressed in any suitable manner, for example, a portion of skin may be clamped or pressed by the receptor. The area of the skin of the subject that is most preferably clamped is an area that is readily drained of blood. Examples, which are not meant to be limiting in any manner, of such an area include loose skin, for example the skin on the wrist, the palm, the neck, or the lobe of the ear. Examples of a receptor that can clamp an appropriate area of skin include receptors shaped as tweezers, tongs; or as a vice or pin, such as a spring-clamp. However, as indicated above, other devices that fit over an arm or leg, or that accept a finger etc. may also be used as described herein.

A receptor of the present invention may also comprise a single sided probe that can make contact with a skin sample. Such a probe may comprise concentric rings of optic fibers so that each ring is made up by fibers carrying either input or output EMR. If the inner ring of fibers is carrying input EMR, then the outer ring of fibers may carry the output signal, or visa versa. This type of probe may be used to determine the concentration of a compound within the skin using reflectance. During use, the probe may be placed against the skin of the hand, arm, back or elsewhere.

Alternate configurations of an apparatus may also be used for the determination of a compound within a part, as described herein, including, but not limited to those described in U.S. Pat. No. 5,361,758, WO 93/16629, U.S. Pat. No. 6,236,047 or 6,040,578 (all of which are incorporated herein by reference). Modification of the calibration algorithms used to determine the concentration of one or more compounds of interest within each body part will be required so as to ensure that a compound within one, or more than one, particular compartment is determined.

The processing system of the device of the present invention determines the oxygen saturation of blood in the part by analyzing the differential absorption of oxygenated hemoglobin, $HbO_2$, and deoxygenated hemoglobin, Hb in arterial blood. Based on the absorbances of the wavelengths of light in the visible red and infrared spectra, the system can calculate a value of arterial oxygen saturation ($Sp_aO_2$) of hemoglobin in the blood of the subject. The system can distinguish hemoglobin absorption from absorption of other components of the tissues within the part based upon the pulsatile nature of arterial blood. In a particular example, the processing system comprises a pulse oximeter.

Figure 2:
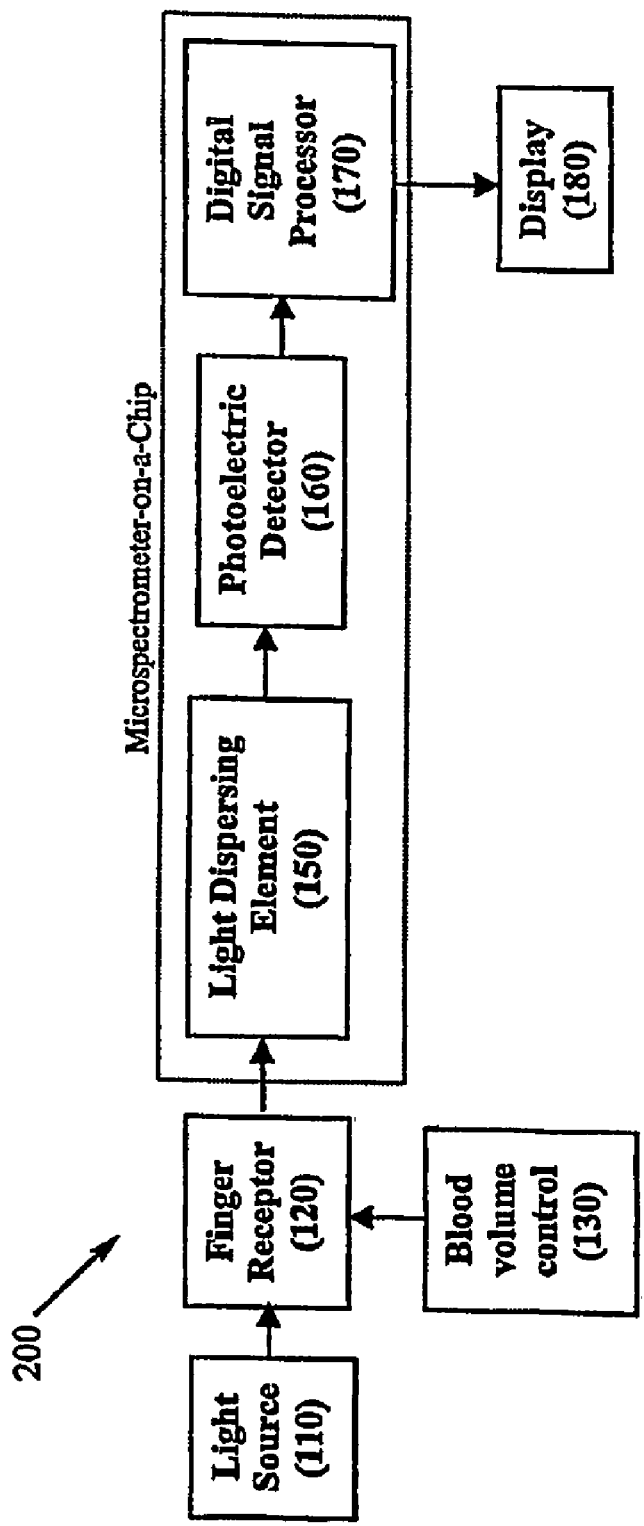

Referring to FIGS. 1-2, there are shown simplified block diagrams of examples of a device (100, 200) according to the present invention, for measuring the concentration of one or more than one compound and a value of oxygen saturation of blood in a finger of a subject. The device (100, 200), which is not to be considered limiting, includes a source of EMR, for example, a polychromatic, or monochromatic light source (10, 110) and a blood volume control (30, 130), which are operatively associated with a receptor for receiving a body part (20,120), for example, a receptor shaped in size to receive a finger. The EMR source (10, 110) may emit a wavelength of light in the visible red spectrum, a wavelength a light in the infrared spectrum and a broad spectrum of light in the near infrared spectrum. The blood volume control (30, 130) measures a value of blood volume in the finger of the subject or a pulse of the subject. The finger receptor (20, 120) includes one or more than one input in operative association with the light source (10, 110) and one or more than one out output in operative association with a combination of a slit (40) and grating (50) or a light dispersing element (150).

The device (100, 200) may also include a photoelectric detector (60, 160) for measuring transmitted or reflected light received from the grating (50) or the light dispersing element (150), a signal processor (70) or a digital signal processor (170) operatively connected to the detector (60, 160), and a display (80, 180). The signal processor (70) or the digital signal processor (170) has one or more than one calibration algorithm for determining a concentration for the one or more than one compound and the value of oxygen saturation of blood in the finger of the subject, and an algorithm for controlling the detector (60, 160) based on the value of blood volume or the pulse measured by the blood volume control (30, 130). The display (80, 180) may be a printer or a visual display screen showing the concentration of the one or more than one compound in the blood of the subject, and the oxygen saturation level of blood in the subject.

The combination of the light dispersing element (150), the photoelectric detector (160) and the digital signal processor (170) shown in FIG. 2 may form part of a microchip, i.e., a microspectrometer-on-a-chip as described, for example, in U.S. Pat. Nos. 5,991,023 and 6,002,479, the disclosures of which are incorporated herein by reference.

Figure 3:
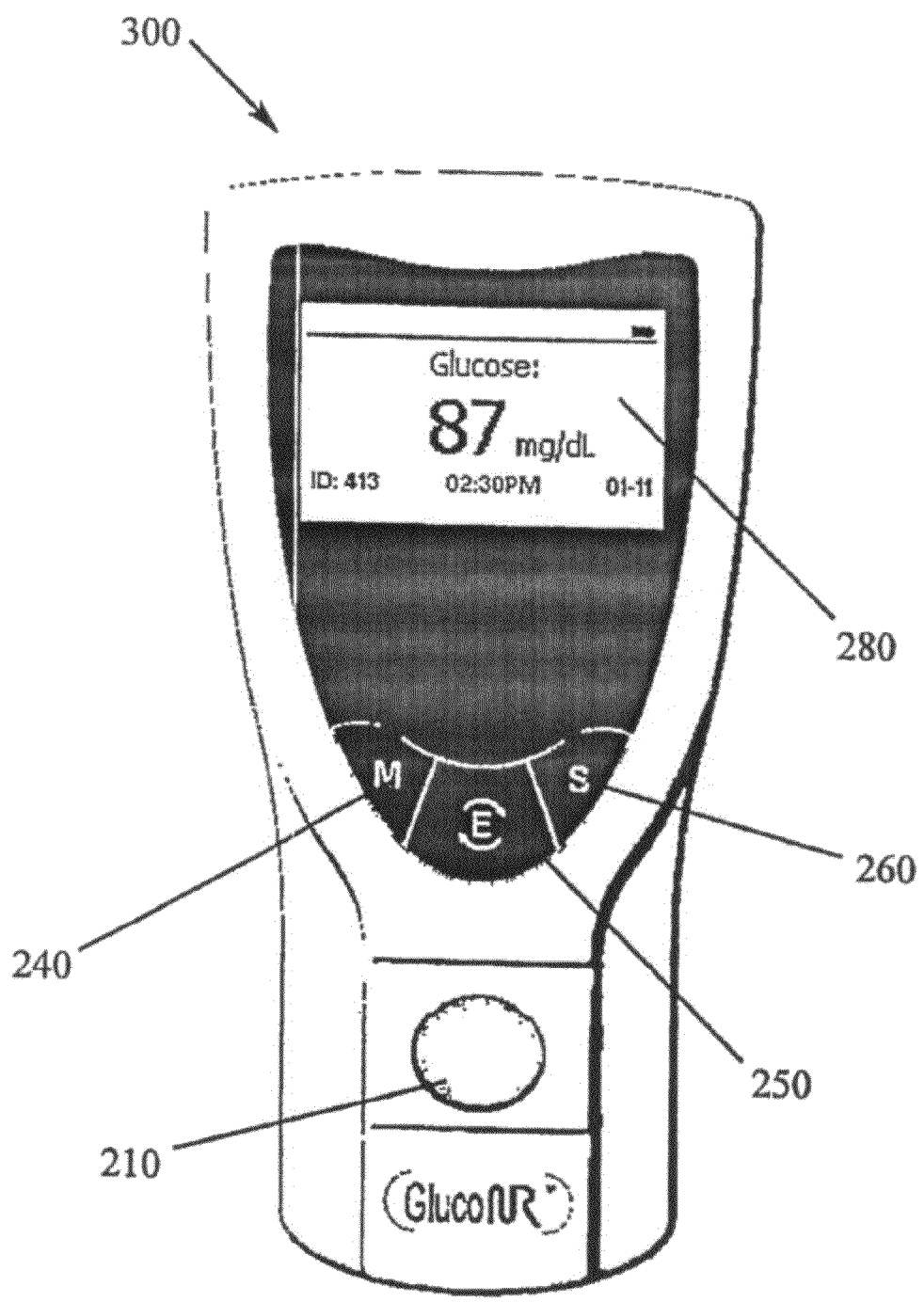
FIG. 3 illustrates an example of a handheld device according to the present invention, which measures both a concentration of one or more compounds and a value of oxygen saturation of blood in a part of a subject.

Referring to FIG. 3, there is illustrated a non limiting example of a handheld device (300) according to the present invention, which may be used to measures both a concentration of one or more compounds and a value of oxygen saturation of blood in the finger of a subject. The device includes the specific components generally illustrated in FIGS. 1-2 and described above. More specifically, the device includes a finger receptor (210) for holding the finger of the subject in a light path defined by the one or more than one input and the one or more than one output, which are in operative association with the polychromatic light source (10, 110) and the combination of the slit (40) and grating (50) or the light dispersing element (150), respectively, a set of input keys (240, 250, 260) for controlling the device (300), and a display screen (280) showing the output of the device, such as the glucose concentration or oxygen saturation level of the blood.

The present invention also provides a method to develop an algorithm that accounts for the differences in concentration of a compound within various compartments of a part of the body that lies along the light path emitted, and received by, the receptor or probe. For example, the concentration of a compound within each of the blood, the interstitial fluid, and the cellular compartment may be determined using any suitable method for example, but not limited to direct measurement of the compound within each compartment, or by using non-invasive techniques, for example nuclear magnetic resonance, and determining the total concentration of the compound within the part of the body. From these values a reference measurement for the compound in the part of the body may be determined, and this reference value used to develop an algorithm for use in determining the concentration of the compound within a part of the body as described herein. Absorbance values of a part of a body may be obtained over a set of wavelengths set as a dependant variable, and glucose reference measurement used as an independent variable.

These values can then be processed using any suitable statistical procedure, including but not limited to, Partial Least Squares or Multiple Linear Regression to produce an algorithm for the compound for a part of the body. This procedure can be repeated for any compound of interest, and for any part of the body, for which a body concentration of the compound is desired.

In the case of glucose, as an example, and which is not to be considered limiting, blood glucose levels can be readily determined using in vitro techniques as known in the art. The level of glucose in the interstitial compartment may be determined using reverse ionotophoesis (e.g. Tierney, M. J., et al. 2000, Electroanalysis 12:666; Potts, R. O. et al. 2002, Diabetes/Metabolism Research Reviews 18:s49-s53), Intercellular glucose concentrations may be determined using any suitable method, for example but not limited to microprobe analysis, for example using a microprobe (e.g. as available from MiniMed) to sample the glucose concentration within a cell. These values may then be used to determine a reference glucose value for the part of the body assayed.

The measurement of the concentration of a compound of the value of oxygen saturation of blood within a part of a body may also change as a result of the change in volume of different compartments within the part of the body. This change in volume may either result in an underestimation or an over estimation of the concentration of the compound. For example, subjects with edema are characterized as having an increased interstitial volume. Therefore, in some instances, it may be desired to correct for changes in volume of the part of the body that is being sampled as described herein. In this instance, the volume of the part of the body may be determined prior to or during determination of the concentration of the compound within the part of the body. However, in many cases, the volume of the part of the body may be predetermined and this value used as a constant with the algorithm in the determination of the concentration of a compound or the value of oxygen saturation of blood within a part of the body.

Therefore, the present invention provides a method for determining a concentration of a compound in a part and a value of oxygen saturation of blood of a part of a subject, comprising:

(a) directing a broad spectrum of electromagnetic radiation (EMR) from the near-infrared spectrum onto the part;

(b) measuring a quantity of EMR reflected by, or transmitted through the part with a detector; and (c) performing a quantitative mathematical analysis of the quantity of EMR using an algorithm that accounts for concentration of the compound within one, or more than one compartment, and the volume of the part; and (d) determining the concentration of the compound in the part and the value of oxygen saturation of the blood in the part.

The present invention also provides a method for determining the concentration of a compound in one or more than one compartment and a value of oxygen saturation of blood of a part of a human or animal, comprising:

(a) directing a broad spectrum of electromagnetic radiation (EMR) from the near-infrared spectrum onto the part;

(b) measuring a quantity of EMR reflected by, or transmitted through the part with a detector; and (c) performing a quantitative mathematical analysis of the quantity of EMR to determine the concentration of the compound in each of the one or more than one compartment and the value of oxygen saturation of blood in the part.

In order to more accurately determine the measurement of a compound of interest within a body part (as a total of all compartments), or to correct the measurement for the presence of the compound within each of the non-target compartments within the part, calibration algorithms specific for the compound within each compartment can be developed. These compound-compartment specific algorithms may be used to either correct for the occurrence of the compound in a non-target compartment, to ensure a proper estimation of the compound in all compartments, or both. Therefore, the present invention is also directed to providing algorithms for use within specific compartments. For example, which is not to be considered limiting in any manner, an algorithm may be developed for the determination of blood glucose, another algorithm for determining interstitial glucose, and another for cellular glucose.

The spectra of a compound may vary within different compartments due to the environment of the compound, or the relative concentration of the compound within the compartment. If the concentration of a compound within a compartment changes, or the relative amount of a compound changes with respect to other compounds within the compartment, the spectra of that compound may change. Without wishing to be bound by theory, such changes may arise from intermolecular associations, reduced molecular mobility, conformational changes and the like. Using this change in the spectral properties of a compound within each compartment, the occurrence of the compound within each compartment can be determined, and the relative contribution of the compound in each compartment, to the total amount of compound, can be analyzed.

In an average male, about 60% of the weight is water. In terms of volume, this is about 42 L, where about 23 L are intracellular and about 19 L are extracellular. Of the extracellular fluid, the plasma accounts for about 3 L and the interstitial fluid accounts for about 8 L. In summary, the largest fluid compartment contains the lowest glucose concentration. The proportion of fluid in the different compartments vary according to several factors including height, weight, age and gender. For an individual, variation occurs due to several factors including physical activity and hormone levels.

For example, which is not to be considered limiting in any manner, in the non-invasive determination of blood glucose concentration, levels of glucose within the interstitial compartment and vascular compartments are very similar due to rapid exchange of small molecules between these two compartments due to diffusion, but intracellular glucose is low because the glucose is readily metabolized. As glucose concentrations increase in blood, for example, when insulin levels are low or the effect of insulin is low, dehydration occurs as follows: When the blood glucose exceeds about 10 mmol/L, the kidney can no longer reabsorb the glucose, resulting in osmotic diuresis and a urine with elevated glucose concentration. The fluid is first lost from the vascular compartment, followed by the intistitial fluid, and finally the intracellular fluid—the body attempts to normalize the blood volume. The increase of glucose in non-target compartments can interfere with the measurement of blood glucose levels. Similarly, it may be desired to be able to determine an increase in interstitial glucose, or cellular glucose levels as an indicator of a medical condition, for example low insulin levels.

The present invention also provides a method for determining a corrected concentration of a compound in a compartment and a corrected value of oxygen saturation of blood of a part of a subject, comprising:

(a) directing a broad spectrum of electromagnetic radiation (EMR) from the near-infrared spectrum onto the part;

(b) measuring a quantity of EMR reflected by, or transmitted through the part with a detector;

(c) performing a quantitative mathematical analysis of the quantity of EMR using an algorithm for the compound within the compartment, and an algorithm for the value of oxygen saturation of blood; and (d) determining the corrected concentration of the compound in the compartment, and the corrected value of oxygen saturation of blood, of the part.

In an alternate embodiment, the relative increase or decrease in the concentration of a compound within a compartment may be determined by monitoring the change in a second metabolite (a marker analyte) that is known to change as a result of a modification within the compartment. For example, in the case of dehydration, dehydration-induced changes in a marker analyte alters the spectra of the analyte. These changes may arise due to conformational changes in the analyte, for example a protein, due to the changes in its aqueous environment, and associated intermolecular interactions (e.g. Carpenter J. F. et al., 1994, pp 134, in Cleland J., Langer R., eds. Formulation and Delivery of Protein and Peptides", Amer. Chem Soc.). Changes in the spectra of a marker analyte may then be used as an indicator of the dehydration state of the compartment, and the relative contribution of the compartment-specific effect of the compound of interests to the total measurement of the compound in the part, may then be determined.

Preferred examples of compounds that are measured within a part, and within different compartments, according to the present invention are selected from the group consisting of a fat, a protein, a glycoprotein, a lipoprotein, a carbohydrate (e.g. glucose), a steroid (e.g. cholesterol), an amino acid, nitrogen, carbon dioxide, cortisol, creatine, creatinine, a ketone, a lipid, urea, a fatty acid, glycosolated hemoglobin, alcohol, lactate, $Ca^{2+}$, $K^+$, $Cl^-$, $HCO_3^-$; $HPO_4^-$, low density lipoprotein, high density lipoprotein, BNP, troponin T and C-reactive protein. Preferably the compound is glucose, however, it is to be understood that the concentration of any desired compound may be determined within different compartments as described herein.

The present invention uses a correlation step to relate the measurements of transmitted or reflected light to a concentration value for one, or more than one, given compound in each of the compartments and a value of oxygen saturation of blood in a part of a subject. If desired, the measured concentration of the compound may be related to a particular parameter such as a clinical condition in need of treatment. The correlation steps used in the methods of this invention may involve several steps of linear regression analysis.

The concentration of a given compound is preferably calculated according to the present invention by using a calibration equation derived from a statistical analysis, for example but not limited to a least squares best fit, of a plot of the values of concentration of a calibration set of samples of the compound, which are determined using the method of the present invention, versus the values of the concentration of the calibration set measured directly by a different method. However, it is to be understood that other statistical tests may be used was known in the art, for example but not limited to multiple linear regression (MLR), partial least squares (PLS), and the like. Any known method for determining the concentration of one, or more than one, compound may be used as would be known to one of skill in the art.

The near infrared region of the electromagnetic spectrum is generally considered to be the spectral interval extending from 650 nm through to 2700 nm and measurements of samples as described herein are preferably taken in the about 700 nm to about 1100 nm range. Absorption bands observed in this interval are primarily the combination and overtone bands of the fundamental infrared bands. Although very weak in intensity, being typically less than one-tenth in intensity of the fundamental infrared bands, these bands are considered to be analytically useful because nearly all chemical species exhibit characteristic absorption bands in this spectral interval. The near infrared region is particularly well-suited to in vivo diagnostic applications because human tissue is essentially transparent to the incident radiation and therefore sufficient penetration of the radiation is possible to allow accurate quantitative analysis.

The source of EMR used in the present invention to detect the compound in the part is preferably near-infrared light, for example but not limited to a polychromatic light source. This type of light source can emit light over a very wide bandwidth including light in the near infrared spectrum. In this case, the light from the light source preferably passes first through a collimator, which is a collection of lenses that concentrate the light into a narrow parallel beam directed at the receptor.

The polychromatic light source can comprise a quartz-halogen or a tungsten-halogen bulb to provide the broad spectrum of light in the near infrared, and is powered by a stabilized power source, for example, a DC power supply, or by a battery. This polychromatic light source may be a tungsten-halogen lamp or it may be a collection of LEDs or other light sources selected to emit radiation in the range of about 650 to about 1100 nm. More particularly, the polychromatic light source comprises a source of light that emits a wavelength of light in the visible red spectrum, for example, 660 nm, a wavelength of light in the infrared spectrum, for example, 940 nm, and a broad spectrum of light in the near infrared region.

In a particular example, the polychromatic light source comprises a pair of light emitting diode emitters to provide light at the wavelengths of 660 nm and 940 nm for detecting the value of oxygen saturation of blood in the part, and a broadband light source that emits a broad spectrum of light in the near infrared. The light emitting diodes and the broadband light sources may be activated simultaneously, or sequentially so that the concentration of the compound in the part and the value of oxygen saturation in the blood within the part are either determined simultaneously, or in a step-wise manner. In addition, the light emitting diodes may be cycled on and off, many times per second, during the process of acquiring absorbance or transmission data to help eliminate background noise.

A receptor is preferably used which is shaped to receive a part of the subject for sampling, for example a clamped part of the skin, or a finger. Alternatively, the receptor could be shaped so that the part of the human or animal, onto which the EMR is to be directed, is placed near the receptor rather than within the receptor. In any event, the sampled part of the skin should be in close contact with the receptor.

The receptor may have means for eliminating extraneous light. For example, where a finger is the part of a human through which the light passes, the receptor may have an oblong shape similar to but larger than the shape of the finger. The means for eliminating extraneous light from the receptor may be a flexible ring that surrounds an entrance to the receptor. When the finger is inserted, the flexible ring forms a seal around the finger when the finger has been inserted into the receptor. In addition, separate seals may be formed within the receptor to help isolate light paths defined between separate sources of light emitting different wavelengths or ranges of wavelengths of light and a detector, to prevent interference between the light emitted from the separate sources of light. Furthermore, all surfaces within the device, including surfaces within the receptor are made non-reflective to minimize stray light.

The EMR is directed onto, and dispersed by, a part of the subject. The dispersed light from the body part, either reflected, transmitted, or both, is collected by using any suitable method, for example, fiber optics, or lenses, and the output signal directed to a diffraction device that separates the wavelengths of light within the output signal into their component parts. Examples of a diffraction device include but are not limited to a diffraction grating or a holographic grating.

The collected signal can comprise EMR that has passed through a part of a subject, or has reflected off of a part of the subject, or a combination thereof. Preferably, the collected EMR has passed through the sample. The diffracting device preferably disperses the EMR into its component wavelengths so that the infrared region falls along the length of a detector such as, but not limited to a linear array detector (e.g. a 256 element photo diode array), or a CCD. In the case of an array, the detector has a series of diodes and is preferably electronically scanned by a microprocessor to measure the charge accumulated on each diode, the charge being proportional to the intensity of EMR for each wavelength transmitted through or reflected from the part of the subject in the receptor. The detector is connected to the microprocessor, producing an output spectrum, with the microprocessor analyzing the measurements and ultimately producing a result for each concentration level determined. The result can be stored, shown on a display, or printed on a printer. A keyboard allows a user to control the device, for example, to specify a particular constituent to be measured. The timing and control is activated by the microprocessor to control the device, for example, to determine number and timing of measurements.

After measurements are obtained for the transmittance, reflectance or both, the log of the inverse of these measurements is preferably taken, that is, log 1/T and log 1/R, where T and R represent the transmittance and reflectance respectively. A reference set of measurements is taken of the incident light, being the light generated in the device when no part of the subject is in contact with the receptor. The absorbance is then calculated when a part of the subject is in contact with the receptor as a ratio of measurements compared to the reference set of measurements.

The second derivative of the measurements is preferably taken in order to reduce any variation in the result that will be caused by a change in path length for the light caused by measuring the compound concentration in different thicknesses of the parts of the subject. While there are other means of manipulating the data obtained from the measurements of reflectance and transmittance, which will produce the same results as those obtained by taking the second derivative, the taking of the second derivative is the preferred means.

As the results obtained can vary with the temperature of the part of the subject, the device used in the method of the present invention preferably contains a temperature sensor so that the temperature of the analyzed part can be measured rapidly at the time of the spectral sampling. This temperature sensor is typically a small-mass thermocouple. Computer software can then be used to allow the microprocessor to compensate for spectrum deviations due to the temperature. So as not to delay the production of results, the temperature sensor preferably has a 150 to 200 millisecond response time.

The linear array detector is preferably a photo diode array that is positioned to intercept, across its length, the dispersed spectrum from the diffraction grating. The microprocessor is directed by software to scan the linear array detector and calculate the second derivative of the spectrum computed. The microprocessor can then calculate the concentration of the particular constituents being measured using the absorbance and second derivative values for a number of selected wavelengths. A calibration equation is preferably used for each constituent and is determined by the compound being measured.

The use of the second derivative calculation also eliminates base line shifts due to different path lengths or absorbing water bands, and in addition, enhances the separation of overlapping absorption peaks of different constituents of the mixture being analyzed.

The microprocessor can collect up to one hundred spectra and can then immediately calculate the second derivative of the averaged results. Preferably, the results will be digitally displayed for the user. Also, by using the memory capacity of the microprocessor, a user can monitor trends by comparing the most recent result with previous results.

The microprocessor may activate and scan the detector only after a detected pulse has occurred and full or partial spectrum measurement can then be taken for the light after it passes through the receptor. Scanning can then be stopped when another pulse is detected. In other words, measurements may be taken only when the blood pressure in the finger or ear or other part of the subject is at a constant level. This ensures that the path length of the tissue through which the light passes is uniform. Pulse detection can be accomplished by conventional means including monitoring plethysmographic volume (i.e. use of light or pressure detection means to monitor changes in volume of the body part) or by sonograms of heart activity or electrocardiograms. If the processing system of the device of the present invention comprises a pulse oximeter, the pulse detection may be performed by the pulse oximeter itself, rather than by a separate device for detecting the pulse of the subject.

While the device of the present invention can be designed to measure one constituent, the device can also be designed to measure several constituents simultaneously.

The above description is not intended to limit the claimed invention in any manner, furthermore, the discussed combination of features might not be absolutely necessary for the inventive solution.

The present invention has been described with regard to preferred embodiments. However, it will be obvious to persons skilled in the art that a number of variations and modifications can be made without departing from the scope of the invention as described herein.

The Embodiments of the Invention in which an Exclusive Property of Privilege is claimed are Defined as Follows:

1. A device for measuring a concentration of one or more than one compound within one or more than one tissue compartment of a body part of a subject, and a value of oxygen saturation of blood in the part of the subject, comprising:
    a polychromatic light source that emits a wavelength of light in the visible red spectrum, a wavelength of light in the infrared spectrum and a broad spectrum of light in the near infrared range from 650 nm to 2800 nm, the light source being operatively coupled to a power source;
    a receptor for receiving the part of the subject and comprising one or more than one input in operable association with the polychromatic light source, one or more than one output in operable association with a dispersing element, the one or more than one input and the one or more than one output defining a light path within the receptor, wherein, the part of the subject when received by the receptor is placed within the light path;
    a pulse detector in operable association with the receptor for detecting a pulse within the part of the subject; and
    a detector for measuring transmitted or reflected light received from the dispersing element, the detector operatively coupled to a processing system;
    the processing system configured to determine the concentration of the one or more than one compound in each of the one or more than one tissue compartments of the body part based on a calibration algorithm that accounts for the concentration of the one or more than one compound within one or more than one compartment, and the value of oxygen saturation of blood in the part, the processing system further configured to use measurements taken immediately subsequent to the detection of a pulse and prior to a next pulse so that all measurements upon which the concentration is based are taken between pulses.

2. The device according to claim 1, wherein said processing system comprises an oximeter.

3. The device according to claim 1, wherein the detector is a linear array detector.

4. The device according to claim 1, wherein the dispersing element is a grating.

5. The device according to claim 1, wherein the compound is selected from the group consisting of a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, $Ca^{2+}$, $K^+$, $Cl^-$, $HCO_3^-$ and $HPO_4^-$.

6. The device according to claim 1, wherein said one, or more than one output comprises a lense, a fibre optic or a hologram.

7. The device according to claim 1, further comprising a collimator between said polychromatic light source and said receptor so that light from the polychromatic light source passes through said collimator before passing into said receptor.

8. The device according to claim 1, wherein the near infrared region in which measurements are taken extends from 700 m to 1100 nm.

9. A method for determining a concentration of one or more than one compound within one or more than one tissue compartment of a body part of a subject, and a value of oxygen saturation of blood in the part of the subject, comprising:
    (a) directing a wavelength of light in the visible red spectrum, a wavelength of light in the infrared spectrum and a broad spectrum of light in the near infrared range (EMR) from 650 nm to 2800 nm onto the part;
    (b) detecting a pulse in the body part of the subject;
    (c) measuring a quantity of EMR reflected by, or transmitted through the part with a detector immediately subsequent to the detection of a pulse and prior to a next pulse so that all measurements upon which the concentration is based are taken between pulses;
    (d) applying a calibration algorithm that accounts for concentration of the compound in each of the one or more than one tissue compartment of the body part; and
    (e) determining the concentration of the one or more than one compound in each of the one or more than one tissue compartment of the body part and the value of oxygen saturation of blood in the part.

10. The method according to claim 9, wherein the compound is selected from the group consisting of a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, $Ca^{2+}$, $K^+$, $Cl^-$, $HCO_3^-$, $HPO_4^-$, high density lipoprotein and low density lipoprotein.

* * * * *